United States Patent [19]

Katsumata et al.

[11] Patent Number: 5,484,716

[45] Date of Patent: Jan. 16, 1996

[54] PROCESS FOR PRODUCING L-TRYPTOPHAN BY A CORYNEBACTERIUM STRAIN HAVING DECREASED PHOSPHOENOLPYRUVATE CARBOXYLASE ACTIVITY

[75] Inventors: Ryoichi Katsumata, Machida; Kuniki Kino, Hofu, both of Japan

[73] Assignee: Kyowa Hakko Kogyo Co., Ltd., Tokyo, Japan

[21] Appl. No.: 130,995

[22] Filed: Oct. 4, 1993

Related U.S. Application Data

[63] Continuation of Ser. No. 625,699, Dec. 12, 1990, abandoned, which is a continuation of Ser. No. 317,589, Mar. 1, 1989, abandoned.

[30] Foreign Application Priority Data

Mar. 4, 1988 [JP] Japan .................. 63-51358
Sep. 27, 1988 [JP] Japan .................. 63-241688

[51] Int. Cl.$^6$ ........................................ C12P 13/22
[52] U.S. Cl. ........................................ 435/108; 435/252.1
[58] Field of Search .............................. 435/108, 843, 435/840, 252.1

[56] References Cited

U.S. PATENT DOCUMENTS

| 4,742,007 | 5/1988 | Kino et al. | 435/252.1 |
| 4,757,009 | 7/1988 | Sano et al. | 435/320 |
| 5,275,940 | 1/1994 | Kino | 435/108 |

FOREIGN PATENT DOCUMENTS

| 0263515 | 4/1988 | European Pat. Off. . |
| 0264914 | 4/1988 | European Pat. Off. . |

OTHER PUBLICATIONS

Herrmann et al, "Amino Acids Biosynthesis and Genetic Regulation", 1983, Addison Wesley, p. 420.
Goodfellow et al, "The Biology of the Actinomycetes" 1984, Academic Press, pp. 77–79.

*Primary Examiner*—Irene Marx
*Attorney, Agent, or Firm*—Antonelli, Terry, Stout & Kraus

[57] ABSTRACT

The invention relates to a bacterial process for producing L-tryptophan, L-tyrosine or L-phenylalanine. The process utilizes a coryneform glutamic acid-producing bacterium being capable of producing L-tryptophan, L-tyrosine or L-phenylalanine and also decreased or lacked in phosphoenolpyruvate carboxylase activity. The mutant strain is then cultured in order to accumulate the amino acid in a medium and the amino acid is recovered therefrom.

1 Claim, No Drawings

PROCESS FOR PRODUCING L-TRYPTOPHAN BY A CORYNEBACTERIUM STRAIN HAVING DECREASED PHOSPHOENOLPYRUVATE CARBOXYLASE ACTIVITY

CROSS-REFERENCE TO RELATED APPLICATIONS

This application is a continuation of application Ser. No. 07/625,699, filed on Dec. 12, 1990, now abandoned, which application is a continuation of application Ser. No. 07/317,589, filed on Mar. 1, 1989 (now abandoned).

BACKGROUND OF THE INVENTION

This invention relates to a process for producing L-tryptophan, L-tyrosine or L-phenylalanine by fermentation. L-tryptophan is an amino acid useful as a medicament, food, an additive for animal, feed, etc.; L-tyrosine is an amino acid useful especially as a medicament; and L-phenylalanine is an amino acid useful in the pharmaceutical and food industries.

Heretofore, various processes for producing L-tryptophan by fermentation using coryneform glutamic acid-producing bacteria have been known; for example, a process using a microorganium belonging to the genus Corynebacterium, requiring L-tyrosine and L-phenylalanine and being resistant to at least of tyrosine analogues and phenylalanine analogues (Japanese Published Examined Patent Application No. 19037/1976); a process using a microorganism resistant to tryptophan analogues, such as 5-methyltryptophan (Japanese Published Examined Patent Application Nos. 18828/1973, 38795/1976 and 39517/1978); a process using a microorganism requiring histidine (Japanese Published Examined Patent Application No. 4505/1972); and a process using a Brevibacterium strain whose pyruvate kinase activity is decreased or lacked (Japanese Published Unexamined Patent Application No. 253391/1987).

Further, various processes for producing L-tyrosine or L-phenylalanine by fermentation using coryneform glutamic acid-producing bacteria have been known; for example, a process using an auxotrophic mutant strain requiring amino acids, a mutant strain resistant to amino acid analogues, a mutant strain whose pyruvate kinase activity is decreased or lacked, or a strain having these properties simultaneously [Nippon Nogeikagaku Kaishi, 50 (1), p.R 79 (1979); Japanese Published Unexamined Patent Application No. 128897/1986].

On the other hand, microorganisms capable of producing L-tyrosine or L-phenylalanine have been constructed by recombinant DNA technique. As an example of L-tyrosine-producing microorganism, a strain carrying a recombinant DNA containing a gene coding for 3-deoxy-D-arabino-hepturosonate-7-phosphate synthase (hereinafter referred to as DS), a gene coding for chorismate mutase (hereinafter referred to as CM) and a gene coding for prephenate dehydrogenase or pretyrosine aminotransferase, is known (Japanese Published Unexamined Patent Application No. 34197/1985). As an example of L-phenylalanine-producing microorganism, a strain carrying a recombinant DNA containing a gene coding for DS or genes coding for CM and prephenate dehydratase (hereinafter referred to as PD), are known (Japanese Published Unexamined Patent Application Nos. 24192/1985, 260892/1986 and 124375/1986).

With the recent increase in the demand for L-tryptophan, L-tyrosine and L-phenylalanine, improved processes for the industrial production thereof are desired.

As a result of intensive studies to obtain a new strain with higher L-tryptophan, L-tyrosine or L-phenylalanine productivity, the present inventors have found that if strains of coryneform glutamic acid-producing bacteria that are capable of producing L-tryptophan, L-tyrosine or L-phenylalanine are mutated to be decreased or lacked in phosphoenolpyruvate carboxylase (EC. 4.1.1.31) (hereinafter referred to as PC) activity, they acquire high productivity of these amino acids.

SUMMARY OF THE INVENTION

This invention provides a process for producing L-tryptophan, L-tyrosine or L-phenylalanine, which comprises culturing in a medium a coryneform glutamic acid-producing bacteium being capable of producing L-tryptophan, L-tyrosine or L-phenylalanine and also decreased or lacked in PC activity, and recovering L-tryptophan, L-tyrosine or L-phenylalanine accumulated in the culture broth therefrom.

DETAILED DESCRIPTION OF THE INVENTION

The coryneform glutamic acid-producing bacterium herein referred to is a microorganism belonging to the genus Corynebacterium or Brevibacterium.

As the mutant strains of the present invention, all the coryneform glutamic acid-producing bacteria that are capable of producing L-tryptophan, L-tyrosine or L-phenylalanine and also decreased or lacked in PC activity can be used. The mutant strains of the present invention can be derived from any coryneform glutamic acid-producing bacterium. Examples of the suitable parent strains are as follows.

| *Corynebacterium glutamicum* | ATCC13032 |
| *Corynebacterium acetoacidophilum* | ATCC13870 |
| *Corynebacterium herculis* | ATCC13868 |
| *Corynebacterium lilium* | ATCC15990 |
| *Brevibacterium flavum* | ATCC14067 |
| *Brevibacterium lactofermentum* | ATCC13869 |
| *Brevibacterium divaricatum* | ATCC14020 |
| *Brevibacterium thiogenitalis* | ATCC19240 |

L-tryptophan-producing strains can be derived from the above coryneform glutamic acid-producing bacteria by imparting requirements for tyrosine and phenylalanine and/or resistance to tryptophan analogues such as 5-methyltryptophan thereto. An example of the L-tryptophan-producing strain is *Corynebacterium glutamicum* ATCC 21851.

L-tyrosine-producing strains can be derived from the coryneform glutamic acid-producing bacteria by imparting requirements for L-phenylalanine and/or resistance to amino acid analogues thereto, or by introduction of a recombinant DNA that contains genes coding for DS, CM, and prephenate dehydrogenase or pretyrosine aminotransferase (Japanese Published Unexamined Patent Application No. 34197/1985). Furthermore, the L-tyrosine-producing strains can also be obtained by introducing, into an L-tryptophan-producing microorganism, a recombinant DNA comprising a DNA fragment involved in the genetic information of enzymes participating in the biosynthesis of L-tyrosine, such as DS and CM, and thereby converting the L-tryptophan-producing strain into an L-tyrosine-producing strain (Japanese Published Unexamined Patent Application No. 94985/1988).

L-phenylalanine-producing strains can be derived from the coryneform glutamic acid-producing bacteria by imparting requirements for L-tyrosine and/or resistance to amino acid analogues thereto, or by introduction of a recombinant DNA that contains genes coding for DS, or CM and PD (Japanese Published Unexamined Patent Application Nos. 24192/1985, 260892/1986 and 124375/1986). Furthermore, L-phenylalanine-producing strains can also be obtained by introducing, into an L-tryptophan-producing microorganism, a recombinant DNA comprising a DNA fragment involved in the genetic information participating in the synthesis of DS, CM and PD, and thereby converting the L-tryptophan-producing microorganism into an L-phenylalanine-producing strain (Japanese Published Unexamined Patent Application No. 105688/1988).

The L-tryptophan-, L-tyrosine- or L-phenylalanine-producing microorganisms whose PC activity is decreased or lacked can be obtained from a known L-tryptophan-, L-tyrosine- or L-phenylalanine-producing strain through mutation that causes such a change in PC activity. Alternatively, the microorganisms of the present invention can also be obtained by imparting auxotrophy and/or resistance to amino acid analogues to a mutant strain whose PC activity is decreased or lacked.

The microorganisms whose PC activity is decreased or lacked may be obtained by mutagenizing cells with conventional methods, for example, ultraviolet irradiation and treatment with chemical mutagens such as N-methyl-N'-nitro-N-nitrosoguanidine (hereinafter referred to as NTG) and nitrous acid, followed by isolation as an L-glutamic acid requiring strain. A mutant strain decreased in PC activity may also be isolated as a strain more sensitive to an affinity labeling reagent of the enzyme, or as a prototrophic revertant of the L-glutamic acid-requiring strain lacking PC activity. The affinity labeling reagent, which is also called active-site-directed irreversible inhibitor, is a compound capable of specifically binding to the active center of an enzyme and thereby inactivating the catalytic activity.

Examples of the strain whose PC activity is decreased or lacked are *Corynebacterium glutamicum* BPS-13 which is capable of producing L-tryptophan, *Corynebacterium glutamicum* K77 which is capable of producing L-tyrosine, and *Corynebacterium glutamicum* K78 which is capable of producing L-phenylalanine.

Production of L-tryptophan, L-tyrosine or L-phenylalanine by a microorganism of the present invention can be carried out in a conventional manner used for the production of amino acids. Either a synthetic medium or a natural medium can be used so long as it contains carbon sources, nitrogen sources, inorganic substances, growth factors, and the like.

As the carbon sources, carbohydrates such as glucose, glycerol, fructose, sucrose, maltose, mannose, starch, starch hydrolyzate and molasses; polyalcohols; and various organic acids such as pyruvic acid, fumaric acid, lactic acid and acetic acids may be used. Hydrocarbons and alcohols may also be used, depending on the assimilability of the microorganism to be used. Of these, cane molasses is preferably used.

As the nitrogen sources, ammonia; various organic and inorganic ammonium salts such as ammonium chloride, ammonium sulfate, ammonium carbonate and ammonium acetate; urea and other nitrogen-containing compounds; and nitrogen-containing organic compounds, such as peptone, NZ-amine, meat extract, yeast extract, corn steep liquor, casein hydrolyzate, fish meal or its digested product are appropriate.

As the inorganic compounds, mention is made of potassium monohydrogen phosphate, potassium dihydrogen phosphate, ammonium sulfate, ammonium chloride, magnesium sulfate, sodium chloride, ferrous sulfate, manganese sulfate and calcium carbonate.

Culturing is carried out under aerobic conditions by shaking culture, aeration-stirring culture, etc. The preferred culturing temperature is generally from 20° to 40° C. The pH of the medium is maintained at around neutrality. The culturing time is generally in the range from 1 to 5 days. L-tryptophan, L-tyrosine or L-phenylalanine can be isolated from the culture by removing the microbial cells through filtration or centrifugation, and recovering the amino acid from the filtrate or supernatant according to known procedures, such as crystallization by concentration, treatment with active charcoal and treatment with an ion-exchange resin.

The following Examples will further illustrate the present invention.

Example 1: Isolation of a mutant strain whose PC activity is decreased (1) L-Tryptophan-producing strain

*Corynebacterium glutamicum* ATCC21851 capable of producing L-tryptophan was used as the parent strain. It was cultured in a complete medium (a medium containing 20 g/l powdered bouillon and 5 g/l yeast extract in water; pH 7.2) at 30° C. for 16 hours. The cells collected were washed with 0.05M phosphate buffer solution (pH 7.2) and suspended in the above-mentioned buffer solution to a concentration of $10^9$ cells/ml. NTG was added to this suspension to a final concentration of 500 µg/ml, and the mixture was held at 30° C. for 20 minutes. The cells thus treated were washed with the above-mentioned buffer solution and spread on a minimal agar medium having a composition shown in Table 1, further containing 0.5 µg/ml 3-bromopyruvic acid (hereinafter referred to as 3BP), which is a compound known as an affinity labeling reagent for PC [J. Biochem., 86, 1251–1257 (1979)].

TABLE 1

| Composition of Minimal Agar Medium | |
|---|---|
| Glucose | 10 g/l |
| $(NH_4)H_2PO_4$ | 1 g/l |
| KCl | 0.2 g/l |
| $MgSO_4 \cdot 7H_2O$ | 0.2 g/l |
| $FeSO_4 \cdot 7H_2O$ | 10 mg/l |
| $MnSO_4 \cdot 4\text{-}6H_2O$ | 0.2 mg/l |
| $ZnSO_4 \cdot 7H_2O$ | 0.9 mg/l |
| $CuSO_4 \cdot 5H_2O$ | 0.4 mg/l |
| $Na_2B_4O_7 \cdot 10H_2O$ | 0.09 mg/l |
| $(NH_4)_6Mo_7O_{24} \cdot 4H_2O$ | 0.04 mg/l |
| Biotin | 0.05 mg/l |
| p-Aminobenzoic acid | 2.5 mg/l |
| Thiamin hydrochloride | 1 mg/l |
| L-Tyrosine | 50 mg/l |
| L-Phenylalanine | 50 mg/l |
| Agar | 16 g/l |
| | (pH 7.2) |

Culturing was carried out at 30° C. for 5 to 10 days, and smaller colonies were picked up from the colonies grown on the plate medium. Strains more sensitive to 3BP than the parent strain were then selected, and a strain whose PC activity was decreased, Corynebacterium glutamicum BPS-13, was finally isolated from the mutant strains sensitive to 3BP.

This strain was deposited on Mar. 2, 1988 with the Fermentation Research Institute, Agency of Industrial Science and Technology, Japan (FRI), under deposition number of FERM BP-1777.

The sensitivity to 3BP of the parent strain ATCC21851 and of the mutant strain BPS-13, and their activities of PC and pyruvate kinase (hereinafter referred to as PK) were shown in Table 2. The 3BP sensitivity was evaluated by spreading each of the two strains on the minimal agar medium having the composition shown in Table 1, further containing different concentrations of 3BP, culturing the strain at 30° C. for 4 days, and observing the degree of growth. The PC activity and PK activity were measured by the method described in J. Biochem., 66 (3), 297–311 (1969) and Agric. Biol. Chem., 48 (5), 1189–1197 (1984), respectively, using crude cell extracts. The crude cell extracts were prepared according to the procedure given below. Each of the strains was inoculated to a medium (pH 7.2) containing 30 g/l glucose, 0.5 g/l $MgSO_4 \cdot 7H_2O$, 10 mg/l $FeSO_4 \cdot 7H_2O$, 1 g/l $KH_2PO_4$, 1 mg/l $MnSO_4 \cdot 4H_2O$, 4 g/l ammonium sulfate, 2 g/l urea, 50 µg/l biotin, 2.5 mg/l p-aminobenzoic acid, 1 mg/l thiamin hydrochloride, 50 mg/l sodium chloride, 50 mg/l L-tyrosine and 50 mg/l L-phenylalanine, and subjected to shaking culture at 30° C. for 24 hours. The grown cellos were collected, washed twice with 0.2% aqueous potassium chloride solution, suspended in 0.1M Tris-HCl buffer solution (pH 7.5), and disrupted by ultrasonic waves. The resulting mixture was centrifuged, and the supernatant was dialyzed overnight against the above-mentioned buffer solution to obtain the crude cell extract. The values shown in Table 2 are given by calculating the specific activity per unit amount of protein contained in the crude extracts, and obtaining the relative value when the specific activity for the parent strain is defined as 100.

TABLE 2

| Strain | Concn. of 3BP (µg/ml) | | | | | PC (%) | PK (%) |
|---|---|---|---|---|---|---|---|
| | 0 | 1 | 3 | 10 | 30 | | |
| ATCC21851 (Parent strain) | ++ | ++ | + | ± | − | 100 | 100 |
| BPS-13 (FERM BP-1777) | ++ | ± | − | − | − | 25 | 138 |

(2) L-Tyrosine-producing strain

Corynebacterium glutamicum ATCC21851 capable of producing L-tryptophan was transformed with recombinant plasmid pCDS-CM1 containing DS and CM genes as described in Japanese Published Unexamined Patent Application No. 94985/1988, and Corynebacterium glutamicum T6 strain (ATCC21851/pCDS-CM1) capable of producing L-tyrosine was isolated according to the procedure described in the same patent application as mentioned above. That is, the ATCC21851 strain was cultured in NB medium (a medium containing 20 g/l powdered bouillon and 5 g/l yeast extract in water; pH 7.2). Then, 4 ml of the seed culture thus obtained was inoculated to 40 ml of semi-synthetic medium SSM [a medium containing 20 g/l glucose, 10 g/l $(NH_4)_2SO_4$, 3 g/l urea, 1 g/l yeast extract, 1 g/l $KH_2PO_4$, 0.4 g/l $MgCl_2 \cdot 6H_2O$, 10 mg/l $FeSO_4 \cdot 7H_2O$, 0.2 mg/l $MnSO_4 \cdot 4-6H_2O$, 0.9 mg/l $ZnSO_4 \cdot 7H_2O$, 0.4 mg/l $CuSO_4 \cdot 5H_2O$, 0.09 mg/l $Na_2B_4O_7 \cdot 10 H_2O$, 0.04 mg/l $(NH_4)_6 Mo_7O_{24} \cdot 4H_2O$, 30 µg/l biotin and 1 mg/l thiamin hydrochloride in water; pH 7.2] further containing 100 µg/ml each of L-tyrosine and L-phenylalanine, and shaking culture was carried out at 30° C. The optical density (OD) at 660 nm was determined with a Tokyo Koden colorimeter and when the OD reached 0.2, penicillin G was added to a final concentration of 0.5 unit/ml. Shaking culture was further continued until OD reached 0.6. The microbial cells were collected, and suspended to a final concentration of about $10^9$ cells/ml in 10 ml of RCGP medium [a medium containing 5 g/l glucose, 5 g/l casamino acid, 2.5 g/l yeast extract, 3.5 g/l $K_2HPO_4$, 1.5 g/l $KH_2PO_4$, 0.41 g/l $MgCl_2 \cdot 6H_2O$, 10 mg/l $FeSO_4 \cdot 7H_2O$, 2 mg/l $MnSO_4 \cdot 4-6H_2O$, 0.9 mg/l $ZnSO_4 \cdot 7H_2O$, 0.04 mg/l $(NH_4)_6Mo_7O_{24} \cdot 4H_2O$, 30 µg/l biotin, 2 mg/l thiamin hydrochloride, 135 g/l disodium succinate and 30 g/l polyvinyl pyrrolidone (M.W.: 10,000) in water; pH 7.6] further containing 1 mg/ml lysozyme. The suspension thus obtained was transferred to an L-type test tube and gently shaken at 30° C. for 5 hours to induce protoplasts.

The resulting protoplast-suspension (0.5 ml) was taken into a small test tube, and centrifuged for 5 minutes at 2,500×g, and the protoplasts collected were suspended in 1 ml of TSMC buffer solution (10 mM $MgCl_2$, 30 mM $CaCl_2$, 50 mM Tris and 400 mM sucrose; pH 7.5) and washed by centrifugation. The protoplasts were resuspended in 0.1 ml of TSMC buffer solution. Then, 10 µl of TSMC buffer solution containing 1 µg pCDS-CM1 plasmid DNA was added to the suspension, and 0.8 ml of TSMC buffer solution containing 20% PEG6000 (Nakarai Chemicals) was further added. Then, 2 ml of RCGP medium (pH 7.2) was added 3 minutes after, and the mixture was centrifuged for 5 minutes at 2,500×g, to remove a supernatant. The precipitated protoplasts were suspended in 1 ml of RCGP medium. The suspension thus obtained (0.2 ml) was spread on RCGP agar medium (RCGP medium containing 1.4% agar; pH 7.2) further containing 400 µg/ml spectinomycin, and cultured at 30° C. for 7 days. The strain grown on the agar medium was isolated as a transformant.

Corynebacterium glutamicum T6 strain thus obtained (ATCC21851/pCDS-CM1) was subjected to mutation in the same manner as described in Example 1 (1), and L-tyrosine-producing Corynebacterium glutamicum K77 strain whose PC activity was decreased was isolated as a 3BP-sensitive mutant strain. The K77 strain was deposited on Sep. 21, 1988 with FRI under deposition number of FERM BP-2062. 3BP-sensitivity, PC activity and PK activity of parent strain T6 and mutant strain K77 were measured in the same manner as in Example 1 (1). The results are given in Table 3.

TABLE 3

| Strain | Concn. of 3BP (µg/ml) | | | | | PC (%) | PK (%) |
|---|---|---|---|---|---|---|---|
| | 0 | 1 | 3 | 10 | 30 | | |
| T6 (parent strain) (ATCC21851/pCDS-CM1) | ++ | ++ | + | ± | − | 100 | 100 |
| K77 (FERM BP-2062) | ++ | + | − | − | − | 36 | 102 |

(3) L-phenylalanine-producing strain

L-phenylalanine-producing Corynebacterium glutamicum T17 strain (ATCC21851/pEaroG-pheA3) was obtained by transforming L-tryptophan-producing *Corynebacterium glutamicum* ATCC21851 with the recombinant plasmid pEaroG-pheA3 containing DS, CM and PD genes of *Escherichia coli* as disclosed in Japanese Published Unexamined Patent Application No. 105688/1988 in the same manner as in Example 1 (2), except that RCGP-agar medium containing 200 μg/ml kanamycin was used for the screening of transformant.

L-phenylalanine-producing *Corynebacterium glutamicum* T17 strain (ATCC21851/pEaroG-pheA3) thus obtained was subjected to mutation in the same manner as in Example 1 (1), and L-phenylalanine-producing for *Corynebacterium glutamicum* K78 strain whose PC activity was decreased was isolated. The K78 strain was deposited on Sep. 21, 1988 with FRI under deposition number of FERM BP-2063. 3BP-sensitivity, PC activity and PK activity of parent strain T17 and mutant strain K78 were measured in the same manner as in Example 1 (1). The results are given in Table 4.

TABLE 4

| Strain | Concn. of 3BP (μg/ml) | | | | | PC (%) | PK (%) |
|---|---|---|---|---|---|---|---|
| | 0 | 1 | 3 | 10 | 30 | | |
| T17 (parent strain) (ATCC21851/ pEaroG-pheA3) | ++ | ++ | + | ± | − | 100 | 100 |
| K78 (FERM BP-2063) | ++ | ± | − | − | − | 22 | 96 |

Example 2

(1) Production test of L-tryptophan

*Corynebacterium glutamicum* BPS-13 (FERM BP-1777) was inoculated in a 300-ml Erlenmeyer flask containing 20 ml of a seed medium (2% glucose, 1.5% polypeptone, 1.5% yeast extract, 0.25% sodium chloride, 0.1% urea, 200 mg/l L-tyrosine and 200 mg/l L-phenylalanine; pH 7.2), and shaking culture was carried out at 30° C. for 24 hours on a rotary shaker set at 210 rpm. The seed culture thus obtained (2 ml) was then inoculated in a 300-ml Erlenmeyer flask containing 20 ml of a fermentation medium of the following composition, and cultured for 72 hours under the same conditions as above. The parent strain ATCC21851 was also cultured as control in the same manner as described above. After culturing, each of the culture flitrates was subjected to paper chromatography and after color formation with ninhydrin, the amount of L-tryptophan produced was measured by colorimetric quantitative determination.

The result is shown in Table 5.

Composition of fermentation medium: 6% glucose, 0.05% $KH_2PO_4$, 0.05% $K_2HPO_4$, 0.025% $MgSO_4 \cdot 7H_2O$, 2% ammonium sulfate, 30 μg/l biotin, 10 mg/l $MnSO_4 \cdot 7H_2O$, 0.5% corn steep liquor and 2% $CaCO_3$ (pH 7.2)

TABLE 5

| Strain | Amount of L-tryptophan produced (mg/ml) |
|---|---|
| ATCC21851 (parent strain) | 6.0 |

TABLE 5-continued

| Strain | Amount of L-tryptophan produced (mg/ml) |
|---|---|
| BPS-13 (FERM BP-1777) | 7.8 |

(2) Production test of L-tyrosine

*Corynebacterium glutamicum* K77 (FERM BP-2062) was inoculated in a 300-ml Erlenmeyer flask containing 20 ml of a seed medium (2% glucose, 1.5% polypeptone, 1.5% yeast extract, 0.25% sodium chloride and 0.1% urea; pH 7.2), and shaking culture was carried out at 30° C. for 24 hours on a rotary shaker set at 210 rpm. The seed culture thus obtained (2 ml) was then inoculated in a 300-ml Erlenmeyer flask containing 20 ml of a fermentation medium having the same composition as in Example 2 (1), and cultured for 72 hours under the same conditions as mentioned above. Separately, the parent strain T6 (ATCC21851/pCDS-CM1) was also cultured as control in the same manner.

After culturing, the culture broth thus obtained (1 ml each) was admixed with 50 μl of 6N-NaOH solution, and heated at 65° C. for 5 minutes to completely dissolve the L-tyrosine precipitated. The culture filtrate was subjected to paper chromatography and after color formation with ninhydrin, the amount of L-tyrosine produced was measured by colorimetric quantitative determination.

The result is shown in Table 6.

TABLE 6

| Strain | Amount of L-tyrosine produced (mg/ml) |
|---|---|
| T6 (ATCC21851/pCDS-CM1) | 4.5 |
| K77 (FERM BP-2062) | 5.8 |

(3) Production test of L-phenylalanine

*Corynebacterium glutamicum* K78 (FERM BP-2063) and its parent strain T17 (ATCC21851/pEaroG-pheA3) were cultured in the same manner as in Example 2 (2). After culturing, each of the culture filtrates was subjected to paper chromatography and after color formation with ninhydrin, the amount of L-phenylalanine produced was measured by colorimetric quantitative determination.

The result is shown in Table 7.

TABLE 7

| Strain | Amount of L-phenylalanine produced (mg/ml) |
|---|---|
| T17 (ATCC21851/pEaroG-pheA3) | 4.8 |
| K78 (FERM BP-2063) | 6.0 |

What is claimed is:

1. A process for producing L-tryptophan, which comprises culturing in a medium a mutant strain having decreased phosphoenolpyruvate carboxylase activity compared to the parent strain thereof, and recovering L-tryptophan accumulated in the culture broth therefrom; said mutant strain being *Corynebacterium glutamicum* BPS-13(FERM BP-1777).

* * * * *